US00PP23528P2

(12) United States Plant Patent
Stemkens

(10) Patent No.: US PP23,528 P2
(45) Date of Patent: Apr. 9, 2013

(54) ***LAVANDULA* PLANT NAMED 'LAAZ0001'**

(50) Latin Name: *Lavandula angustifolia*
Varietal Denomination: LAAZ0001

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/373,779

(22) Filed: Nov. 29, 2011

(51) Int. Cl.
*A01H 5/00* (2006.01)

(52) U.S. Cl. ..... Plt./445

(58) Field of Classification Search ..... Plt./445
See application file for complete search history.

*Primary Examiner* — Annette Para

(74) *Attorney, Agent, or Firm* — Joshua L. Price

(57) ABSTRACT

A new *Lavandula* plant named 'LAAZ0001' particularly distinguished by the violet-blue flowers, an early season flowering response, individual flowers stay open all day and plant continuously flowers through the entire summer season.

1 Drawing Sheet

Latin name of the genus and species of the plant claimed: *Lavandula angustifolia.*

Varietal denomination: 'LAAZ0001'.

BACKGROUND OF THE NEW PLANT

The present invention comprises a *Lavandula*, botanically known as *Lavandula angustifolia*, and hereinafter referred to by the variety name 'LAAZ0001'.

'LAAZ0001' is a product of a planned breeding program. The new cultivar has violet-blue flowers, an early season flowering response, individual flowers stay open all day and plant continuously flowers through the entire summer season.

'LAAZ0001' originates from a self-pollination made in August 2005 in a controlled breeding program in Enkhuizen, Netherlands. The female parent was an unpatented, proprietary plant identified as 'G3012-13' with lighter blue color, erect growth with less branching.

The resulting seeds were sown in the early spring of 2006 and 'LAAZ0001' was selected as one flowering plant within the progeny of the stated cross in July 2006 in a controlled environment in Enkhuizen, Netherlands.

The first act of asexual reproduction of 'LAAZ0001' was accomplished when vegetative cuttings were propagated from the initial selection in August 2006 in a controlled environment in Enkhuizen, Netherlands.

BRIEF SUMMARY OF INVENTION

Horticultural examination of plants grown from cuttings of the plant initiated in the spring of 2007 in Enkhuizen, and continuing thereafter, has demonstrated that the combination of characteristics as herein disclosed for 'LAAZ0001' are firmly fixed and are retained through successive generations of asexual reproduction.

'LAAZ0001' has not been observed under all possible environmental conditions. The phenotype may vary significantly with variations in environment such as temperature, light intensity and day length.

A Plant Breeder's Right for this cultivar was applied for in the European Union on Apr. 7, 2011, #2011/0899.

'LAAZ0001' has not been made publicly available more than one year prior to the filing of this application.

The following traits have been repeatedly observed and are determined to be basic characteristics of the new variety. The combination of these characteristics distinguishes this *Lavandula* as a new and distinct variety.

BRIEF DESCRIPTION OF THE PHOTOGRAPHS

The accompanying photographic drawing shows typical flower and foliage characteristics of 'LAAZ0001' with colors being as true as possible with an illustration of this type. The photographic drawing shows a flowering plant of the new variety and a close-up of the inflorescence.

DETAILED BOTANICAL DESCRIPTION

The plant descriptions and measurements were taken in Enkhuizen, Netherlands in early July 2011 using plants growing in an outdoor container trial in 13 cm pots. These plants were approximately 20 weeks of age.

The photographs were taken in mid July 2011. The plants used for the photographs were about 24 weeks of age and were grown in a greenhouse trial in Enkhuizen, Netherlands.

Color Chart used: Royal Horticultural Society Colour Chart (R.H.S.) 2001

DIFFERENCES BETWEEN THE NEW VARIETY 'LAAZ0001' AND A SIMILAR VARIETY: 'LABLUSA' U.S. Plant Pat. No. 19,765

| | 'LAAZ0001' | 'Lablusa' U.S. Plant Pat. No. 19,765) |
|---|---|---|
| Flowering response: | Earlier | Later |
| Branching habit: | Stronger/freer branched | Weaker/fewer branching |
| Plant height: | Shorter | Taller |

Plant:

*Form, growth and habit*.—Compact, upright, freely branching.

*Plant height*.—20.0-25.0 cm.

*Plant height* (*inflorescence included*).—About 30.5 cm.

*Plant width*.—About 36.0 cm.

Roots:

*Number of days to initiate roots*.—About 12 days at about 18 degrees C.

*Number of days to produce a rooted cutting*.—3-4 weeks at 18 degrees C.

*Type*.—Fine, fibrous, free branching.

*Color*.—Closest RHS 161D.

Foliage:

*Type*.—Opposite; decussate, sessile.

*Fragrance*.—Strong.

*Immature, leaf color, upper surface*.—RHS 137C.

*Lower surface*.—RHS 137D.

*Mature, leaf color, upper surface*.—RHS 138A.

*Lower surface*.—RHS 139C.

*Length*.—4.0-5.0 cm.

*Width*.—0.8 cm.

*Shape*.—Ligulate.

*Base shape*.—Sessile.

*Apex shape*.—Acute.

*Margin*.—Entire.

*Texture, upper surface*.—Hairy.

*Lower surface*.—Hairy.

*Color of veins, upper surface*.—RHS 143C.

*Color of veins, lower surface*.—RHS 143C.

Stem:

*Number of main stems per plant*.—About 15-25.

*Color of stem*.—RHS N138B.

*Length of stem*.—About 15.0-22.0 cm.

*Diameter*.—0.2 cm.

*Length of internodes*.—2.5-5.5 cm.

*Shape of stem*.—Square.

*Strength*.—Good.

*Texture*.—Hairy.

*Peduncle color*.—RHS N138B.

*Peduncle length*.—About 14.0 cm.

*Peduncle diameter*.—0.2 cm.

*Peduncle strength*.—Strong.

*Peduncle texture*.—Hairy.

Inflorescence:

*Type*.—Flowers in compact spikes, terminal on stems; flowers stay open all day.

*Number of open flowers per inflorescence*.—About 140 in various stages of development.

*Quantity of inflorescences per plant*.—About 20-30.

*Lastingness of individual blooms on the plant*.—About 3 days.

Bud (when first showing color):

*Color*.—RHS 90C.

*Length*.—0.4 cm.

*Width*.—0.3 cm.

*Shape*.—Oval.

Corolla:

*Immature*.—Color of petals, upper surface: RHS 90C. Lower surface: RHS 90C.

*Mature*.—Floret horizontal diameter: 0.5 cm. Floret length: About 3.4 cm. Mature, color of petals, upper surface: RHS 93B, becoming more RHS 93D. Lower surface: RHS 93B, becoming more RHS 93D. Petal length: 0.2 cm. Petal diameter: 0.2 cm. Apex: Obtuse. Margin: Entire. Base: Fused. Degree of lobation: Moderate. Texture, upper surface: Glabrous. Lower surface: Glabrous. Corolla Tube, color, outer surface: RHS 85A and RHS N155B. Color, inner surface: RHS 85A and RHS N155B. Corolla tube length: 0.3 cm. Diameter (at opening): 0.1-0.15 cm. Corolla tube texture, outer surface: Glabrous. Inner surface: Glabrous.

Calyx:

*Form*.—All sepals fused to form tube around the corolla.

*Color*.—RHS N88A.

*Length of tube*.—0.3 cm.

*Width of tube*.—0.2 cm.

*Texture, outer surface*.—Pubescent.

*Inner surface*.—Glabrous.

Reproductive organs:

*Number of stamens*.—4.

*Filament color*.—RHS 155C.

*Filament length*.—0.2 cm.

*Filament diameter*.—0.05 cm.

*Anther color*.—RHS N167A.

*Anther length*.—0.05 cm.

*Anther shape*.—Reniform.

*Pollen color*.—RHS 163B.

*Pollen amount*.—Sparse.

*Pistil*.—1.

*Pistil length*.—0.4 cm.

*Style color*.—RHS 150D.

*Style length*.—0.2 cm.

*Stigma color*.—RHS N199D.

*Fertility/seed set*.—Has not been observed on this hybrid.

*Disease/pest resistance*.—Has not been observed on this hybrid.

What is claimed is:

1. A new and distinct cultivar of *Lavandula* plant named 'LAAZ0001' as substantially illustrated and described herein.

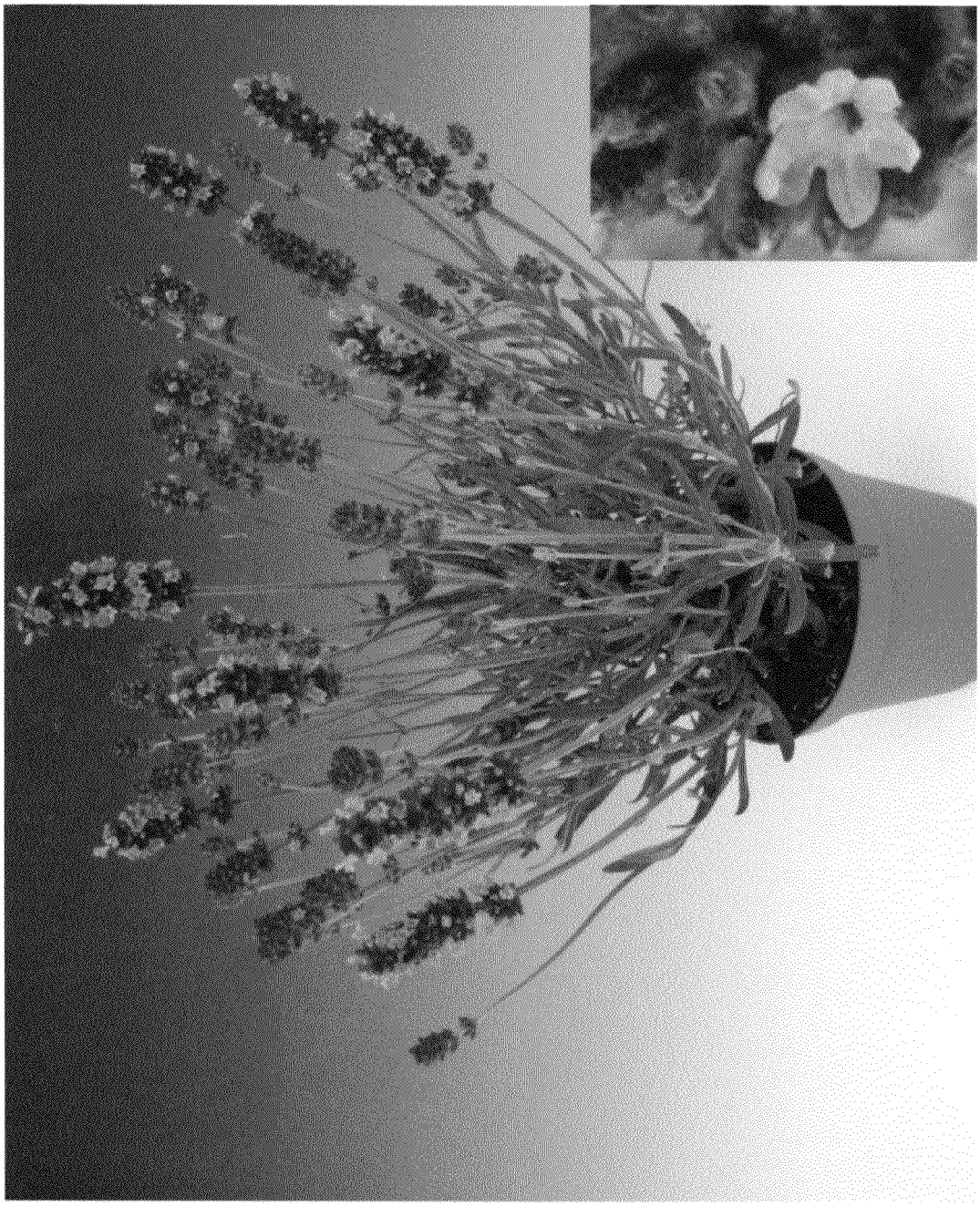

* * * * *